United States Patent [19]

Younes

[11] Patent Number: 5,540,222
[45] Date of Patent: Jul. 30, 1996

[54] PISTON-BASED VENTILATOR DESIGN AND OPERATION

[75] Inventor: Magdy Younes, Winnipeg, Canada

[73] Assignee: University of Manitoba, Winnipeg, Canada

[21] Appl. No.: 107,653

[22] PCT Filed: Feb. 12, 1992

[86] PCT No.: PCT/CA92/00060

§ 371 Date: Oct. 18, 1993

§ 102(e) Date: Oct. 18, 1993

[87] PCT Pub. No.: WO92/14505

PCT Pub. Date: Sep. 3, 1992

[30] Foreign Application Priority Data

Feb. 19, 1991 [GB] United Kingdom ............... 9103419

[51] Int. Cl.$^6$ .................................................. A61M 16/00
[52] U.S. Cl. ............................ 128/205.18; 128/204.21; 128/204.26; 128/205.24; 417/42
[58] Field of Search ............... 128/204.21, 204.23, 128/204.26, 205.18, 205.24; 417/42

[56] References Cited

U.S. PATENT DOCUMENTS

| | | | |
|---|---|---|---|
| 3,918,447 | 11/1975 | Inkster et al. | 128/205.18 |
| 4,336,590 | 6/1982 | Jacq et al. | 128/204.23 |
| 4,587,967 | 5/1986 | Chu et al. | 128/205.18 |
| 4,617,637 | 10/1986 | Chu et al. | 128/205.18 |
| 5,107,830 | 4/1992 | Younes | 128/204.18 |
| 5,265,594 | 11/1993 | Olsson et al. | 128/204.23 |
| 5,365,922 | 11/1994 | Raemer | 128/204.23 |

FOREIGN PATENT DOCUMENTS 1408242  10/1975  United Kingdom ............. 128/204.23

Primary Examiner—Edgar S. Burr
Assistant Examiner—William J. Deane, Jr.
Attorney, Agent, or Firm—Sim & McBurney

[57] ABSTRACT

Improvements in piston-based ventilator design and operation are described. In one aspect, individual compensation of force dissipation within the gas delivery system is effected, so that the desired gas pressure is delivered to the patient airway without the necessity for monitoring the actual pressure and using it as feedback. In another aspect, a piston is dimensioned slightly less than the chamber wall of the pump to define a gap through which an acceptable amount of gas may leak but which eliminates the need for a physical seal, thereby minimizing the frictional resistance within the pump.

14 Claims, 2 Drawing Sheets

PISTON-BASED VENTILATOR DESIGN AND OPERATION

FIELD OF INVENTION

The present invention relates to piston-based ventilators for ventilating the lungs of patients.

BACKGROUND OF THE INVENTION

Commercially-available piston-based ventilators operate to deliver a preset tidal volume at a preset pattern and rate of flow. Several models are available which satisfactorily perform this function. With such ventilators, however, the patient cannot independently influence the flow rate or volume once a cycle is triggered. In certain applications, it is more desirable to utilize ventilators with which the controlled variable is pressure, as opposed to volume or flow, output. Here, the control system of the ventilator is designed to alter pressure according to specified functions. Although this approach does not guarantee a specific tidal volume, it does allow the patient the freedom to influence his/her breathing pattern during the supported breath. This results in greater comfort.

Prior art exists for piston-based ventilator designs which are intended to deliver pressure according to specified functions (e.g. U.S. Pat. No. 4,448,192 to Stawitcke, Younes, J. Applied Physiology 62:2491–2499, 1987). In all these prior art designs, pressure is controlled according to a servo feedback mechanism in which the actual pressure is compared with the desired pressure, an error signal is generated, and this error signal is used to drive the motor which, in turn, alters the pressure in the piston, thereby minimizing the error signal and maintaining the actual pressure as close as possible to the desired function. This approach, however, has two major disadvantages:

1. By definition, an error (difference between actual and desired pressure) must exist in order for the motor to respond. This error theoretically can be minimized by increasing the gain of the error signal. However, because in ventilated patients, pressure in the tubing is invariably highly variable, and because of obligate delays between the generation or change in error signal and the actual change in pressure, a high error gain would be associated with wide fluctuations in the command signal to the motor and hence oscillations. Thus, if the error gain is set such that a difference in pressure of 1 cm $H_2O$ between actual and desired pressure results in a piston pressure output of 30 cm $H_2O$, a relatively small variation in the actual pressure signal (e.g. ±1 cm $H_2O$) would initiate oscillations of considerable amplitudes. This consideration makes it necessary to use relatively low error gain or substantial filtering techniques, both of which result in poor responsiveness of the device. Thus, if a patient pulls harder, which tends to reduce system pressure, the compensation by the device will be slow and incomplete, thereby causing actual pressure to deviate substantially from desired pressure.

2. This type of control makes it progressively more difficult to regulate adequately pressure at points more distal from the piston and, hence, at points closer to the patient. This is because all tubing used to connect piston to patient's airway displays substantial compliance and resistance. There are, therefore, obligate delays in pressure transmission from piston to patient. The farther out (from the piston) the point used for pressure feedback (used to generate the error signal) is located, the greater the delay between a change in piston pressure in response to a change in error signal and those changes being detected at the site used for pressure feedback. This delay would tend to result in the motor overcompensating with a pressure overshoot which, once the overshoot reaches the pressure monitoring site, will unnecessarily reduce the error signal resulting in an undershoot. A tendency for oscillation is again created which is greater the closer the pressure feedback site is to the patient's airway, and also greater the higher the compliance and resistance of the tubing between piston and pressure monitoring site. To offset this instability, the response must be damped with more damping required as the site for pressure control is advanced closer to the patient. Since a more damped control system responds slowly, a conflict, therefore, arises between the need to control pressure as close to the patient as possible and the responsiveness of the ventilator to changes in airway pressure produced, for example, by changes in patient demand.

One aspect of this invention is directed towards solving the servo-feedback problem by employing what is termed herein a "piecemeal" approach to piston control.

All commercially-available piston-based ventilators are currently utilized to deliver predetermined tidal volumes at predetermined flow rates. In other words, they function as volume ventilators. In recent years, there has been a trend away from this type of ventilation to other modalities in which the ventilator delivers pressure at the patient airway according to desired functions. Neither flow nor volume is predetermined as the patient determines these through changes in his own effort. This type of ventilatory support is more comfortable and associated with less risk to the patient. Examples of this type of approach include pressure support ventilation (PSV), in which the ventilator controls pressure at the airway according to specified and predetermined functions of inspiratory time, and the more recent Proportional Assist Ventilation (PAV) as described in U.S. Pat. No. 5,044,362 and in more detail in published European patent application No. 452001 and Younes et al, American Review of Respiratory Diseases, col. 145, pp 114–129, 1992, the disclosures of which are incorporated herein by reference in which delivered pressure is a function of ongoing inspired volume and rate of flow of gas from ventilator to patient. With any of these newer approaches, the patient must be able to freely alter the rate of gas flow while the machine maintains pressure according to the desired function regardless of patient effort, and hence flow rate. At present, these options are commercially-available only on ventilators operated with pneumatic valves which control flow from a high pressure source (e.g. Puritan-Bennett 7200 and Siemens-Elema 900C) and in blower-based ventilators (e.g. Respironic's BiPAP). It would be advantageous to be able to use piston-based ventilators to deliver these newer pressure support options.

In commercially-available piston-based ventilators the chamber is sealed through physical contact between the rim of the piston and inner surface of the cylinder. This design is unsuitable for the delivery of these new pressure support options. This is because the friction between piston and cylinder wall is not only high but non-uniform. The degree of friction varies from one position to the next along the cylinder and from time to time as a result of wear. This variable resistance results in variable dissipation of the force generated by the motor and, hence, variability in the relation between desired and obtained pressures. Servo-feedback using airway pressure can be used to optimize this relation despite the variable friction. However, as indicated earlier, there are serious limitations to the use of the airway pressure feedback to servo-control ventilator pressure output in order to implement these pressure support modalities. For adequate performance in this regard, the friction between piston and cylinder must be minimal.

Rolling seal pistons can be designed such that the friction is negligible. Such pistons have been utilized in prior art devices intended to deliver pressure according to desired functions (e.g. Stawitcke U.S. Pat. No. 4,448,192; Younes et al U.S. Pat. No. 5,044,362. Although rolling seal pistons offer satisfactory performance for the purpose of delivering pressure support options, they have two drawbacks. First, the survival of the sealing diaphragm is influenced by many hardware design features and operating conditions. There is always the risk of unexpected rupture with potentially catastrophic results. Second, with piston ventilators, the gas intake is often not from a pressurized source but simply from the room. The piston must be forcefully retracted in the exhalation phase to refill the chamber with fresh gas. The negative pressure thus created often causes inversion or double convolution of the diaphragm which in turn causes a variable increase in resistance and marked reduction in diaphragm survival.

Another aspect of the present invention is directed towards solving the piston friction problem by designing a piston which has a very low resistance to movement in the piston chamber.

SUMMARY OF INVENTION

In one aspect of the present invention, there is provided a novel method of control of a ventilator which does not employ servo-feedback but rather effects individual compensation for force dissipation occurring both within the ventilator and the tubing.

Accordingly, this aspect of the invention provides a method of operating a ventilator delivering gas to a patient airway and comprising a force generating mechanism and tubing for connecting the force generating mechanism and the patient airway, characterized by effecting individual compensation for force dissipating steps within the force generating mechanism and within the tubing between the force generating mechanism and patient airway, so as to provide a desired gas pressure at the patient airway.

This aspect of the invention further provides a ventilator apparatus for delivering gas by tubing to a patient airway, comprising chamber means operably connected to the tubing and having movable wall means for compressing and decompressing gas therein, electrical motor means operably connected to the movable wall means to apply a motive force to the movable wall means in proportion to the magnitude of an electrical command signal applied to the electric motor means, and electrical circuit means operably connected to the electrical motor means for applying the electrical command signal to the electrical motor means. The electrical circuit means is characterized by comprising (a) electrical circuit means for generating a first electrical signal compensating for force dissipating steps within the chamber means, movable wall means and the electrical motor means, (b) electrical circuit means for generating a second electrical signal compensating for force dissipating steps within the tubing, and (c) electrical circuit means for summing the first and second electrical signals to provide the electrical command signal.

A second aspect of the invention provides a novel ventilator structure which, by reason of its structure, incorporates one or more of the piecemeal compensation steps provided in the first aspect of the invention. Accordingly, in this second embodiment of the invention, there is provided a ventilator apparatus for delivering gas to a patient airway, characterized by chamber means having a smooth and uniform inner surface and piston means mounted for reciprocal movement within the chamber means and having an outer dimension slightly less than the inner dimension of the chamber means to define a small gap therebetween throughout the range of reciprocal movement of the piston means.

DESCRIPTION OF PREFERRED EMBODIMENTS

Referring first to FIG. 1, with all piston-based ventilators, pressure (at the desired site) is ultimately controllede through changes in the force or torque generated by a motor. A wide variety of motors is commercially-available with which there is a fixed relation between current supplied and force, or torque, generated. It is, therefore, a simple matter to reliably produce force or torque of any desired magnitude at any time. The problem is primarily in the conversion of force (or torque) developed by the motor to pressure at the desired site. Numerous mechanical steps, which dissipate force, are interposed between the force generating mechanism in the motor and the site at which pressure is to be controlled. Since the force required by some of these mechanical steps is highly variable, there is no reliable relation between force generated inside the motor and pressure at the desired site.

Figure 1A:
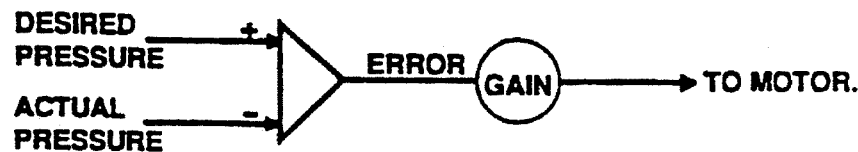
"FIG. 1A is a schematic circuit diagram illustrating servo-feedback control of a motor driving a piston in a ventilator according to the prior art.
Figure 1B:
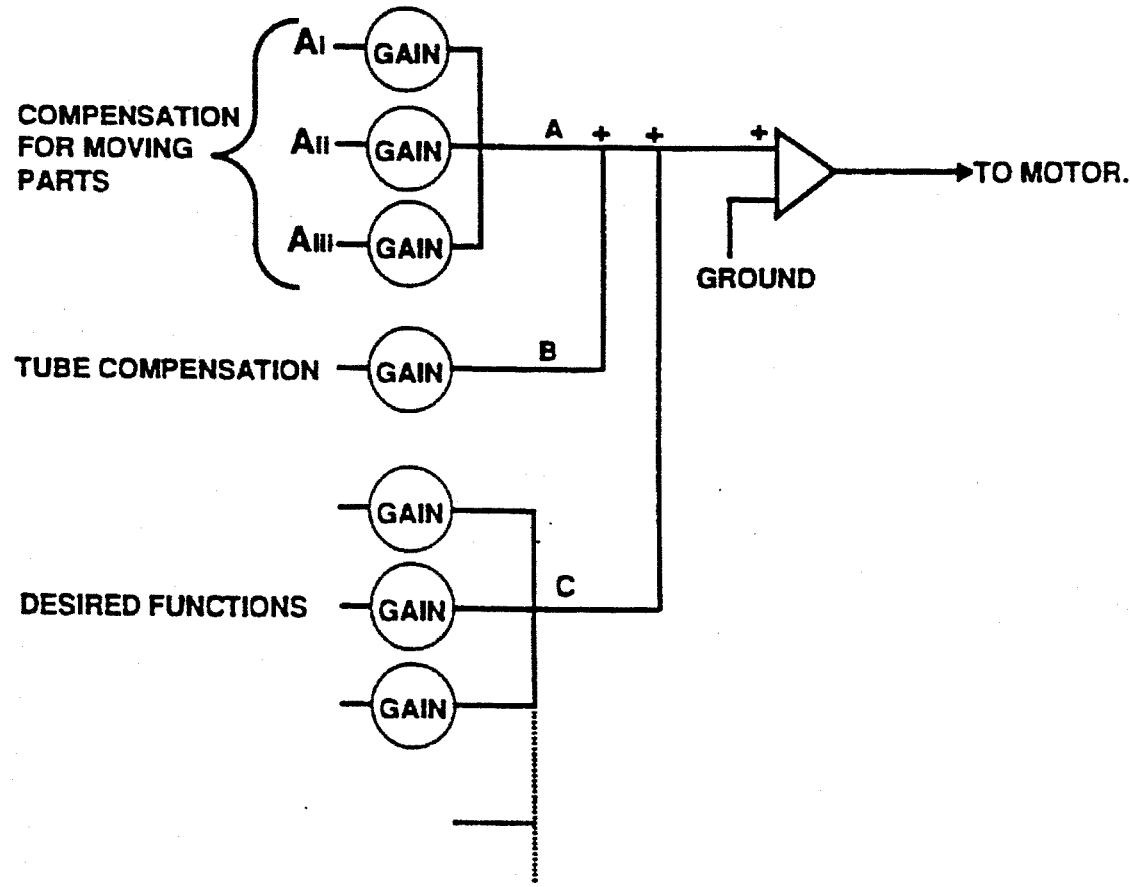
FIG. 1B is a schematic circuit diagram illustrating a piecemeal compensation approach to motor control in accordance with one aspect of the invention.

With pressure servo-feedback system, (as depicted in FIG. 1A), the effect of these intermediate mechanical steps is compensated for through generating an error signal related to the difference between actual and desired pressure. The more force is dissipated by the intermediate steps, the greater the deviation between actual and desired pressure, the greater the error signal and this results in the motor increasing its force appropriately to offset the effect of the intermediate steps. The problems related to this approach, as applied to mechanical ventilation, are outlined above.

With the "piecemeal" approach of the present invention, there is no comparison (i.e. subtraction) of actual and desired pressures and no error signal generated. Rather, the various steps responsible for force dissipation between motor and desired site are identified and the force dissipated at each step is either made negligible through appropriate selection or design of mechanical components or through inputs to the motor that are proportional to the force dissipated by the individual steps. The power supplied to the motor thus is a function of the sum of (and not the difference between) a number of signals, each compensating for a specific step in the force transmission chain. To this signal is added a signal representing the desired pressure function at the selected site. A signal corresponding to pressure at the desired site is not required for implementation of the piecemeal approach, although it can be measured for monitoring purposes.

The mechanical steps that dissipate force are conveniently divided into the following two categories:

Category A: Steps between force generating mechanism in the motor and the chamber being pressurized. These steps also are conveniently divided into the following three categories:

i) Steps dissipating a constant force. These steps include the static friction factor in the motor and some of the moving components (pulleys, gears, etc.);

ii) Steps dissipating force as a function of the rate of motion (viscous friction). The sources of this type of dissipation can exist in any of the moving parts including the motor itself, bearings, belts, etc. However, the most significant potential source is friction between the moving piston (or vane) and the wall of the chamber; and iii) Steps dissipating force as a function of acceleration. This dissipation would occur in the case where moving parts move along the axis of gravity (e.g. the piston moving up and down as opposed to horizontally).

Category B: Pressure dissipation between chamber and site selected for pressure control. This dissipation is primarily related to resistance of the intervening tubing and, therefore, is a function of rate of gas flow in this tubing.

When steps A and B (A and B, FIG. 1) are fully compensated for through direct inputs, and, in the absence of additional inputs representing desired functions (C, FIG. 1), pressure at the selected site is maintained at atmospheric pressure regardless of pattern and magnitude of gas flow into the patient. Additional inputs, representing a desired function (input C, FIG. 1), therefore, result in an appropriate change in pressure at the selected site regardless of pattern or magnitude of flow into the patient and without pressure feedback.

Methods of Compensation

Category A: The steps in category A can be compensated for electrically or through design features that render force dissipation negligible over the operating range of the unit.

Step Ai (static friction) is compensated for electrically using a constant signal. The amplitude of the signal is set to result in the force (torque) required to offset this factor. This component can be minimized mechanically through choice of mechanical parts with very low static friction and/or through design features that greatly increase the torque or force required to alter chamber pressure, thereby rendering static friction a very minor factor relative to overall force required from the motor. This result may be accomplished by using pistons (or moving vanes) with large areas and/or by transmission mechanisms that reduce the force applied to the piston for a given force or torque generated by the motor. These mechanical options, however, all entail a substantial cost in term of expense, motor weight and/or power consumption. Electrical compensation is much simpler.

Force dissipation related to rate of motion (Aii) is offset by providing electrical power to the motor in proportion to a signal representing rate of motion. The latter signal can be derived from a tachometer mounted on the motor, a differentiated signal from a potentiometer or device which measures linear displacement, or from a signal corresponding to the rate of flow of gas out of the chamber. A major problem in the implementation of this step is the requirement that force dissipation due to rate of motion be a fixed function of rate of motion. As indicated earlier, the major component of this resistance is the friction between the moving plate (piston, vane, . . . etc.) and the chamber wall. With designs in which the moving plate comes in contact with chamber wall, a uniform resistance along the entire excursion of the moving plate is nearly impossible to accomplish, as mentioned above. Hence, satisfactory electrical compensation is difficult to achieve then this approach to motor control is utilized, it is highly preferable to utilize chambers in which the seal is not dependent on direct contact between chamber wall and moving plate. Rolling seal designs are particularly suited for this purpose. However, sudden rupture of the seal, with potentially disastrous consequences, would be a source of concern, as stated earlier. The piston design of FIG. 2 and described in more detail below satisfies this requirement, without the risk associated with rolling seals.

Force dissipation related to acceleration (Aiii) can be compensated for electrically by providing an input to the motor that is proportional to acceleration. This component is negligible if the moving parts are oriented to move horizontally. However, this orientation augments the wear on bearings, particularly where the weight of the moving plate is supported by bearings, which is the case in piston designs in which moving plate and cylinder are not in contact, as in the structure illustrated in FIG 2.

Category B: Pressure dissipation in the tubing between cylinder and site of pressure control is accomplished by providing electric current to the motor in proportion to the pressure gradient between the two sites. The pressure gradient can be measured directly by use of a differential transducer with one end connected to the chamber and the other to the site of pressure control. Alternatively, since the pressure gradient is a function of flow from cylinder to patient, the flow signal itself can be used for compensation. In other words, input B may be determined by the relationship $B=f\dot{V}$, where $\dot{V}$ is rate of flow and $f$ is a function describing the pressure-flow relation of the tube. However, since tubes with different resistance properties may be attached to the ventilator, thereby requiring different functions for each tube, and since the resistance of a given tube may vary from time to time due to bending, water condensation or pressure of secretions, the former direct method is preferable.

Category C represents the desired pressure for the purpose of dissipation against the patient and is provided by signals that represent the desired functions. The nature of these functions can vary from application to application (for example, constant pressure, triangular, square or complex wave forms during inspiration (pressure support), pressure in proportion to flow, volume or both (proportional assist . . . etc.).

A ventilator incorporating this piecemeal approach to motor control employs a variety of electrical signals each with its own independent gain control (FIG. 1B), namely Ai, DC signal; Aii, signal proportional to rate of movement; Aiii, signal proportional to acceleration; B, signal proportional to pressure gradient between chamber and pressure control site; and C, signal or signals proportional to desired pressure functions to be applied to patient.

A variety of methods may be used to adjust the different gains to achieve proper compensation. A simple and reliable procedure involves compensation for category A steps first by monitoring pressure in the chamber and withdrawing gas from piston according to the following procedure. All signals are set at zero. Air is withdrawn at a steady but very slow rate. Chamber pressure undergoes a step negative change reflecting the static friction factor (since flow is minimal and unchanging factors ii and iii can be ignored). The gain on Ai signal is increased until pressure remains near zero when the same maneuver is repeated. This step compensates for factor Ai. Air then is withdrawn at a faster, but steady, rate representing nearly the upper limit of flow rate to be encountered in routine use (e.g. 3 L/sec for ventilators designed for adult use). The gain on the Aii signal then is increased until it is found that chamber pressure remains near zero when the procedure is repeated. Finally, air is withdrawn in an accelerating then decelerating pattern, such as by the operator taking a deep inhalation from the chamber. In this case, if inertial losses are significant, chamber pressure will deflect in a negative direction while flow is increasing (early) and then becomes positive as flow is decreasing (late). The gain on Aiii signal then is increased until similar maneuvers elicit no appreciable change in chamber pressure.

Once this procedure is complete, the gains on Ai, Aii, Aiii, need not be changed, except during routine maintenance procedures where minor readjustments may be needed due to change in the mechanical properties of the moving parts as a result of wear.

Following the adjustment of the gains on category A signals, some tubing is attached to the cylinder and the other end of the pressure transducer (i.e. that which is not connected to the chamber) is connected to the distal end of the tube. Air is withdrawn from the free end of the tube at a steady rate and the gain on the B signal is increased until similar maneuvers elicit little change in pressure at the distal end of the tube. Where the direct method of estimating the pressure gradient (between chamber and end of tube) is used, this gain need not be changed except during routine maintenance since compensation takes place regardless of what kind of tube is used. When the indirect method is used, the gain is tube and condition specific and, therefore, requires frequent adjustment. The B gain control in this case preferably is an external one that can be adjusted by the user.

Once the system is adjusted in the above fashion, a calibration factor can be established which represents the pressure that is generated for each volt of additional input. This calibration factor then can be used to set the gains of the various desired functions (Category C).

This novel piecemeal approach to providing a control signal to the drive motor of a piston of a patient ventilator ensures that pressure at the desired site matches the desired pressure in due time, without the need for monitoring the pressure or using it for feedback, and without any potential for oscillations. Some delays, however, are inevitable because of the response time of the motor and the presence of compliant structures between motor and site of pressure control. Particularly during rapid transients, actual pressure may temporarily deviate from desired pressure. The magnitude and duration of these deviations depend on the response characteristics of the motor, the extent of filtering applied to the various electrical signals and the mechanical properties of the chamber and tubing. With proper selection of these variables, the response may be perfectly adequate for most uses. However, additional methods may be employed to expedite the response of pressure to a change in demand.

One of these procedures is to combine the proposed approach with servo pressure feedback. In this case, a signal proportional to pressure is subtracted from one or more components of the command signal to result in an error signal which then serves as an additional input. It must be emphasized that, unlike the usual pressure servo systems in prior art, the error signal in this case is not the primary determinant of power supply to the motor, but is only an option intended to expedite the response and is only significant during transients. Because the role of the error signal is marginal, a low error gain may be used which is consistent with stability even when the pressure monitoring site is far removed from the piston.

In accordance with this first aspect of the present invention, therefore, there is provided a method for the control of pressure at the airway of a patient according to desired functions, which comprises effecting individual (or piecemeal) compensation for various force dissipating steps within the force generating mechanism and between the force generating mechanism and patient airway.

In one embodiment, this method is carried out by apparatus comprising a chamber in which gas is compressed and decompressed through movement of one of its walls, such as a piston or bellows; a motor attached to the moving component of the chamber so that chamber pressure is altered through the action of the motor; electrical circuitry to provide motor with power in proportion to a command signal; and circuitry to generate the command signal which comprises:

circuitry to generate a signal to compensate for static friction, viscous resistance and inertial losses by the moving parts which is composed of a DC signal and/or a signal proportional to rate of movement of moving parts and/or a signal proportional to acceleration of moving parts, and circuitry to generate a signal to compensate for pressure losses between chamber and airway comprising a signal proportional to pressure difference between chamber and airway, and optionally circuitry to generate signals proportional to the desired functions.

Specific features of this embodiment of the invention, which may be used alone or in combination of two or more features, comprise the following:

When the DC component of the command signal intended to compensate for static friction is made unnecessary through use of moving parts with negligible static friction.

Where the component of the command signal related to rate of motion, intended to compensate for viscous friction, is made unnecessary through the use of moving parts with negligible frictional resistance.

Where the component of the command signal related to acceleration, is eliminated through proper orientation of the moving parts or use of light weight moving parts.

Where compensation for resistive pressure losses in the tubing connecting chamber to patient is done indirectly through having a signal which is a function of rate of gas flow from ventilator to patient.

Where a signal proportional to pressure in chamber or anywhere along the tubing is subtracted from one or more components of the command signal for the sake of generating an error signal which, in turn, becomes part of the command signal in addition to, or in lieu of, the components.

Figure 2A:
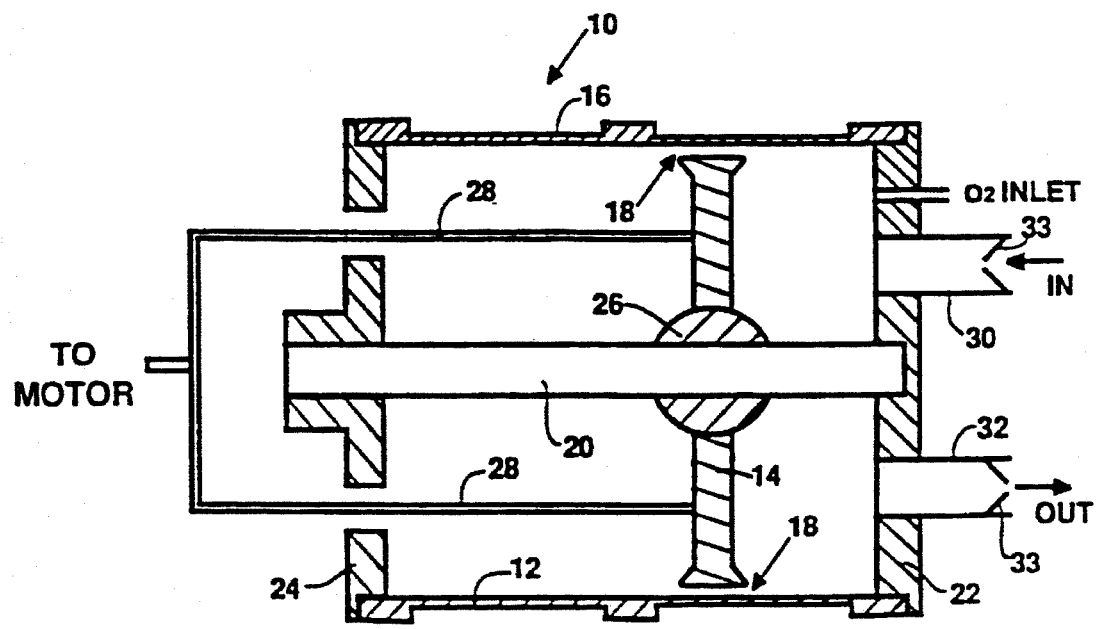
FIG. 2A is a sectional view of a novel piston in a patient ventilator provided in accordance with another aspect of the invention.

Turning now to consideration of FIG. 2, which illustrates a novel design of piston for a ventilator which minimizes friction but yet is able to effectively deliver pressure. In this aspect of the present invention, a very low resistance is maintained by ensuring complete physical separation between piston rim and chamber wall by the use of a piston with a slightly smaller diameter than the internal diameter of the chamber and with appropriate guidance mechanisms to maintain the physical separation between piston and chamber throughout the entire range of piston movement. The difference between piston diameter and chamber internal diameter is selected such that the leak around the piston rim is relatively small, and hence tolerable, at chamber pressures generated during normal use.

Although chambers of various shapes may be provided embodying these principles, a cylindrical chamber 10 is utilized to illustrate the preferred embodiment. Figure 2 shows a longitudinal section of the cylinder 12 and piston 14. The length and internal diameter of the cylinder 12 are selected such that the total volume displaced by piston excursion matches the anticipated maximum tidal volume (e.g. 3 L for an adult ventilator) while also allowing for the anticipated leak during the highest expected pressures. The thickness of the cylinder wall 16 is such that it resists deformation at the prevailing pressures and depends on the material used. The piston 14 is perfectly round and its diameter is slightly smaller than the internal diameter of the cylinder 12, to define a gap 18. This difference is extremely critical, since the magnitude of the leak through the gap 18 is related to the third power of the distance between piston and cylinder. Nonetheless, the differences in diameters required for an acceptable leak is well within the achievable tolerance of modern machining and mould construction. For example, if the thickness of the piston rim is 0.5 inch (1.25 cm), and its circumference is 24 inches ( approximately 8 inch diameter), with a gap 18 of 0.002 inch (50 micrometer) between piston 14 and cylinder 12 (i.e. piston diameter 0.004 inch smaller than cylinder diameter), the leak is approximately 1.2 ml/sec/cm $H_2O$. If the average pressure in the chamber during inspiration is 30 cm $H_2O$ (peak pressure about 60 cm $H_2O$) and inspiration lasts 1 sec, the total leak would be 36 ml which is less than 10% of the tidal volume. In turn, a tolerance of 0.002 inch, or even better, is easily achievable with current construction techniques. Because the magnitude of leak is critically dependent on the width of the gap 18, it is preferable to use the same material for both cylinder wall and piston rim so that both react similarly to temperature changes, thereby maintaining the separation almost constant regardless of temperature.

Because the magnitude of the leak is predictable and is pressure dependent, a pressure dependent correction factor can be applied to the signal representing piston displacement so that the latter can continue to reflect the amount of gas exiting the chamber to the patient tubing. Therefore, an independent method of measuring flow and volume of gas transferred to patient is not required.

A variety of mechanisms may be utilized to ensure that the piston retains its axial position within the cylinder, and hence to ensure there is no frictional engagement between the piston rim and cylinder. These mechanisms may include rails on the inner wall of the cylinder with corresponding notches in the piston or a variety of shaft and bearing designs. In the preferred embodiment, as illustrated, there has been satisfactorily employed a perfectly-centered shaft 20 extending from a front plate 22 to a rear plate 24. The piston glides smoothly along the shaft 20 with the help of a high quality precision bearing 26 mounted in the center of the piston 14. The piston 14 in turn is coupled to the motor using rods 28 that exit through the back plate 24.

The front plate 24 includes openings 30, 32 for intake of air and for connecting ventilator to patient tubing, respectively. Appropriate one-way valves 33 are ordinarily mounted on these openings.

The piston design described above with respect to FIG. 2 may incorporate additional optional features to increase piston stability, for example, an expanded piston rim or appropriately located "feet". Additionally, mechanisms to monitor displacement (e.g. potentiometer), or rate of displacement of piston may be mounted to reflect volume and flow, respectively. A small fan may be included in the chamber to mix gases in the event $O_2$ enriching is carried out by directly injecting oxygen in the chamber where it is mixed with air taken from the room via the intake opening.

Figure 2B:
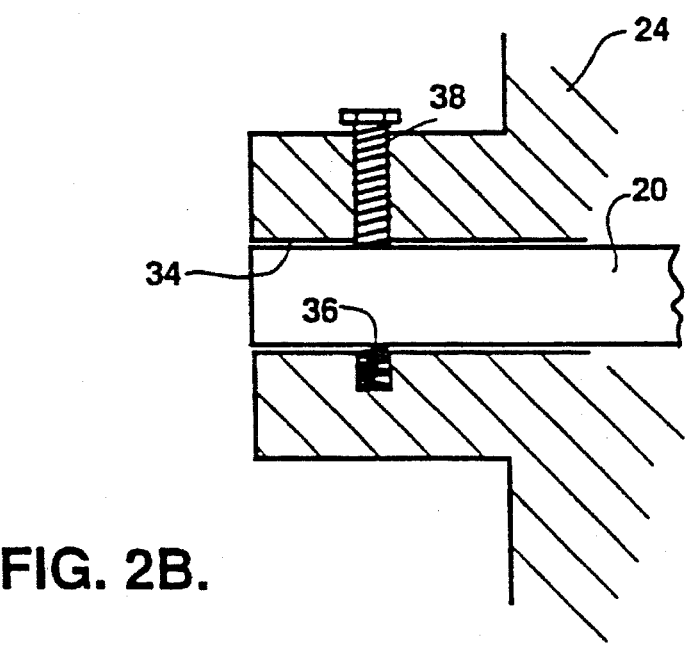
FIG. 2B is a close-up sectional view of a portion of the patient ventilator of FIG. 2A."

An additional modification is shown in FIG. 2B, which permits very fine adjustments of the position of the piston 14 should piston 14 and cylinder 12 come in contact because of wear of bearing 26 or rod 20. The orifices 34 accommodating both the front and back ends of the central shaft (only one end is illustrated) are made slightly larger than the shaft 20 (rod). A spring 36 on one side and a bolt 38 on the counter side can be used to effect fine movement of the rod 20 in one direction (for example, up and down). Similar mechanisms can permit fine adjustments in other directions (e.g. side to side).

In accordance with this second aspect of the present invention, therefore, there is provided a novel gas delivery chamber structure for clinical ventilators which is seal-free and piston-based. In one embodiment, the gas delivery chamber comprises a chamber with a smooth and uniform inner surface; a piston which reciprocates within the chamber and whose outer dimensions are slightly smaller than the inner dimensions of the chamber and where the difference between the piston and cylinder dimensions is calculated to result in minimal leak, within the pressure range encountered in clinical use, when piston is properly centered within the chamber; and guidance means, such as guide rails and shafts, to cause the piston to remain in centre of chamber throughout its range of motion.

Specific features of this embodiment of the invention, which may be used alone or in combinations of two or more features, comprise the following:

When equipped with means to monitor displacement and/or rate of motion of piston, particularly when equipped with means to calculate the volume and rate of leak around piston from signals related to chamber pressure and means to subtract the calculated volume and rate of leak from signals related to displacement and rate of displacement of piston, respectively, such that the latter signals, having accounted for the leak around piston, reflect volume and rate of flow exiting the chamber in the direction of patient.

When equipped with inlet tubing for gas intake and exit tubing to be connected to patient, particularly where valves are inserted to cause unidirectional flow from gas source, or room, to chamber via inlet during the exhalation phase and flow from chamber to patient via exit orifice during the inhalation phase.

When additionally equipped with a fan in chamber to facilitate gas mixing.

When equipped with a separate inlet to inject oxygen into chamber.

When equipped with means to periodically readjust piston position within the chamber.

SUMMARY OF DISCLOSURE

In summary of this disclosure, the present invention provides novel methods and structures to achieve improved operation of piston-based ventilators. Modifications are possible within the scope of this invention.

What I claim is:

1. A method of operating a ventilator delivering gas to a patient airway and comprising a force generating mechanism which comprises a chamber, a piston reciprocally movable in said chamber to generate air pressure therein and an electric motor operably connected to said piston to apply a motive force thereto in proportion to the magnitude of an electrical control signal applied to said electric motor means and tubing for connecting said force generating mechanism and the patient airway, which method comprises:

generating a first electrical signal comprising:

a signal of constant predetermined value a signal corresponding to the velocity of said piston, and a signal corresponding to the acceleration of said piston, generating a second electrical signal corresponding to the pressure gradient between said chamber and the patient airway, and generating said electrical control signal comprising the sum of said first and second electrical signals, whereby compensation is effected for force dissipating steps within said force generating mechanism and within said tubing between the force generating mechanism and patient airway, so as to provide a desired gas pressure at the patient airway.

2. The method of claim 1 wherein said desired gas pressure is atmospheric pressure.

3. The method of claim 1 wherein said electrical control signal further comprises an electrical signal of a magnitude corresponding to a desired function to effect a desired change in pressure at the patient airway.

4. The method of claim 1 wherein said chamber has a smooth inner surface and said piston is mounted for reciprocal movement within the chamber and has an outer dimension slightly less than the inner dimension of said chamber to define a small unobstructed gap throughout the range of reciprocal movement of said piston.

5. A ventilator apparatus for delivering gas by tubing to a patient airway, which comprises:

chamber means operably connected to said tubing and having movable wall means for compressing and decompressing gas therein, electrical motor means operatively connected to said movable wall means to apply a motive force to said movable wall means in proportion to the magnitude of an electrical command signal applied to said electric motor means, and electrical circuit means operably connected to said electrical motor means for applying said electrical command signal to said electrical motor means, said electrical circuit means comprising:

electrical circuit means for generating a first electrical signal comprising a signal of constant predetermined value, a signal corresponding to the velocity of said moveable wall means and a signal corresponding to the acceleration of said moveable wall means, electrical circuit means for generating a second electrical signal corresponding to the pressure gradient between said chamber means and the patient airway, and electrical circuit means for summing said first and second electrical signals to provide said electrical command signal.

6. The ventilator apparatus of claim 5 wherein said electrical circuit means further comprises:

electrical circuit means to generate a third electrical signal corresponding in magnitude to effect a desired change in pressure at the patient airway.

7. The ventilator apparatus of claim 5 wherein said chamber means has a smooth uniform inner surface and said moveable wall means comprises piston means mounted for reciprocal movement within the chamber means and having an outer dimension slightly less than the inner dimension of said chamber means to define a small unobstructed gap therebetween throughout the range of reciprocal movement of said piston means.

8. A ventilator apparatus for delivering gas by tubing to a patient airway which comprises:

chamber means operatively connected to said tubing and having a smooth and uniform inner surface, and piston means mounted for reciprocal movement within the chamber means and having a smooth outer wall having a uniform outer dimension slightly less than the inner dimension of said chamber means to define a small unobstructed gap of uniform width between the outer wall of the piston means and the inner surface of the chamber means throughout the range of reciprocal movement of said piston means.

9. The ventilator apparatus of claim 8 wherein said chamber means has an elongate cylindrical shape and said piston means comprises a cylindrical head having said outer dimension.

10. The ventilator apparatus of claim 9 wherein said chamber means comprises a gas inlet opening and an outlet opening in an end closure thereof opposite said piston means, and said inlet opening and outlet opening have unidirectional flow valves operably arranged in connection therewith to permit gas to enter said chamber means through said inlet opening only during reciprocal movement of said piston means away from said end closure and to permit gas to exit said chamber means through said outlet opening and pass to a patient only during reciprocal movement of said piston means towards said one end closure.

11. A ventilator apparatus for delivering gas to a patient airway, which comprises:

chamber means of elongate cylindrical shape and having a smooth and uniform inner surface, and piston means mounted for reciprocal movement within the chamber means and comprising a cylindrical head having an outer dimension slightly less than the inner dimension of said chamber means to define a small unobstructed gap therebetween throughout the range of reciprocal movement of said piston means, said piston means comprising stationary shaft means axially mounted in said chamber means and said cylindrical head being mounted on said stationary shaft means for smooth gliding movement along said shaft.

12. The ventilator apparatus of claim 11 wherein said cylindrical head is connected to drive motor means located externally of said chamber means for reciprocal movement of said cylindrical head within said chamber means.

13. The ventilator apparatus of claim 11 wherein said stationary shaft means is mounted at each end thereof in forwarded and rear closures to said chamber means and wherein the mountings comprise means for altering the position of said shaft relative to said closures.

14. A ventilator apparatus for delivering gas to a patient airway, which comprises:

chamber means having an elongate cylindrical shape and a smooth and uniform inner surface, piston means mounted for reciprocal movement within the chamber means and comprising a cylindrical head having an outer dimension slightly less than the inner dimension of said chamber means to define a small gap therebetween throughout the range of reciprocal movement of said piston means, a gas inlet opening and an outlet opening in an end closure of said chamber means opposite said piston means, said inlet opening and outlet opening having unidirectional flow valves operably arranged in connection therewith to permit gas to enter said chamber means through said inlet opening only during reciprocal movement of said piston means away from said end closure and to permit gas to exit said chamber means through said outlet opening and pass to a patient only during reciprocal movement of said piston means toward said one end closure, and an additional inlet opening is provided in said one end closure for injection of oxygen into said chamber means.

* * * * *